US006849429B1

(12) United States Patent
Watowich et al.

(10) Patent No.: US 6,849,429 B1
(45) Date of Patent: Feb. 1, 2005

(54) VIRAL PSEUDO-CAPSIDS INCLUDING ASSEMBLY AGONISTS AND ANTAGONISTS

(75) Inventors: Stanley J. Watowich, Houston, TX (US); Meghan Kunkel, Galveston, TX (US); Marta Lorinczi, Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/713,687

(22) Filed: Nov. 15, 2000

Related U.S. Application Data

(60) Provisional application No. 60/166,556, filed on Nov. 19, 1999.

(51) Int. Cl.[7] ......................... C12N 15/80; C12P 19/34; C12P 13/00; C12P 21/00

(52) U.S. Cl. ................ 435/91.1; 424/185.1; 424/186.1; 424/228.1; 424/205.1; 424/225.1; 435/91.1; 435/91.21; 435/473

(58) Field of Search ................................ 435/235.1, 41, 435/42, 236, 473, 91.1, 57.21; 424/228.1, 205.1, 225.1, 185.1, 186.1, 189.1

(56) References Cited

FOREIGN PATENT DOCUMENTS

WO 98/21338 * 5/1998

OTHER PUBLICATIONS

Falco et al. Tissue & Cell, 1999, vol. 31, pp. 117–125.*
Tellingghuisen et al. J. Virol. 1999, vol. 73, pp. 5309–5319.*
Bother et al. Nature Structural Biology, 1999, vol. 6, pp. 114–116.*
Yusui et al. J. Virol. 1998, vol. 72, pp. 6048–6055.*
Vladimir et al. Virol. 1993, vol. 192, pp. 38–51.*
Thomsen et al. J. General Virol. 1992, vol. 73, pp. 1819–1824.*
Baumert et al. J. Virol. 1998, vol. 72, pp. 3827–3836.*
Baumert et al. J. Virol. 1998, vol. 72, pp. 3827–3836.*
Wengler et al. Virol. 1982, vol. 118, pp. 401–411.*
Lingappa et al. J. Cell Biology. 1994, vol. 125, pp. 99–111.*
Spearman et al. J. Virol. 1996, vol. 70, pp. 8187–8194.*
Platt et al. Pro. Natl. Acad. Sci. USA 1994, vol. 91, pp. 4594–4598.*
Darnell et al. Chapter 3 in Molecular Cell Biology edited by Darnell et al. pp. 83–88.*
Jens Bukh, et al.; Sequence Analysis of the Core Gene of 14 Hepatitis C Virus *Genotypes: Proc. Natl. Acad. Sci. USA* ; Aug. 1994; pp. 8239–8243; vol. 91.
C. Cammarota, et al.; Partial Nucleotide Sequencing of Six Subtype 2c Hepatitis C Viruses Detected in Italy; *Journal of Clinical Microbiology*; Oct. 1995; pp. 2781–2784; vol. 33, No. 10.

* cited by examiner

*Primary Examiner*—James Housel
*Assistant Examiner*—Bao Qun Li
(74) *Attorney, Agent, or Firm*—Gardere Wynne Sewell LLP

(57) ABSTRACT

Recombinant hepatitis C virus (HCV) capsid proteins that self-assemble into large spherical virus-like particles structures and viral capsids that include conformational antigenic epitopes are provided. The large spherical virus-like particles structures and viral capsids, including capsid proteins that are expression products of a viral particle coding sequence protein, may be prepared as vaccines to induce a cellular or humoral immune response. The self assembling capsid proteins may also be used as elements of diagnostic immunoassay procedures for HCV infection.

13 Claims, No Drawings

VIRAL PSEUDO-CAPSIDS INCLUDING ASSEMBLY AGONISTS AND ANTAGONISTS

This application is a conversion from and claims priority of U.S. Provisional Application No. 60/166,556, filed Nov. 19, 1999.

Work resulting in the present invention was supported in part by a United States government grant NIH Pilot Project Grant under DHHS V19 A10035. Accordingly, the government has certain rights in the present invention.

TECHNICAL FIELD OF THE INVENTION

The invention relates to recombinant viral proteins, and more particularly, to recombinant viral capsid proteins and methods that may be used in the development of new antiviral agents.

BACKGROUND OF THE INVENTION

Without limiting the scope of the invention, its background is described in connection with viral capsid proteins and assays for inhibitors of viral assembly, as an example.

Structurally, viruses typically comprise at least a viral genome encapsidated within a proteinaceous shell termed the capsid. During virus assembly, individual constituent capsid proteins of one or more kinds associate with the viral genome in a coordinate fashion and assemble into a three-dimensional nucleocapsid structure. The nucleocapsid may be naked as with the very simple polio viruses or may be enveloped by one or more membranes derived from the host cell as with herpes viruses. Virtually all phases of viral replication are dependant on the biochemical machinery of the infected host cell. As such, few chemotherapeutic agents are available that selectively affect viral replication without considerable host toxicity. What is needed is a system for the generation of new antiviral agents that target unique viral replication events. The need is particularly acute for those viruses that cannot be readily grown in cell culture and thus are not easily amenable to the development of antiviral agents that are both effective and host sparing.

SUMMARY OF THE INVENTION

The present invention is directed in part to the development of antiviral agents that are able to target a step in viral replication that may be considered relatively unique to the infecting virus, the step of assembly of virus encoded proteins into the virus nucleocapsid. Assembly of components into a complete virus particle is a critical step in the generation of new virus particles. Although virus assembly is a theoretical target for antiviral chemotherapeutics, lack of a viable in vitro assay adaptable to high throughput screening has thwarted the development of antivirals directed to blockage of viral assembly. In one embodiment of the present invention, a system for in vitro modeling of eukaryotic virus assembly is provided. Such an in vitro system may be particularly useful in the development of antiviral agents effective against viruses that cannot be grown in cell culture.

An example of one such virus, hepatitis C Virus ("HCV"), has emerged as a major public health threat. The inability to culture the virus in vitro has seriously hampered investigations into structural characteristics of the viral core proteins and the development of effective antivirals. In one aspect of the present invention, a screening method and tool for the development of agents able to inhibit HCV maturation is provided.

HCV is an enveloped, single stranded positive sense RNA virus that has been placed in the Hepacivirus genus of the Flaviviridae family. HCV is a single capsid protein virus in which the nucleocapsid is formed from the assembly of multiples of a single capsid protein that assembles together with the viral genome into a symmetrical geometric three-dimensional array. The term "capsid protein" is not necessarily synonymous with "core protein" as some viruses have additional "core proteins" included within the capsid or nucleocapsid. In the case of HCV however, "core" or "core protein" has been used interchangably with "capsid" or "capsid protein."

Due in part to the inability to cultivate the virus in vitro, the virus was definitively identified by molecular cloning of the viral genome (Choo, et al., Science 244: 359–62, 1989) in 1979. The genome consists of a 5' noncoding region followed by a single open reading frame encoding encoding three structural proteins: a 23 kD nucleocapsid (p22, core) and two envelope glycoproteins (E1, E2), and four nonstructural proteins (NS2, NS3, NS4, NS5) extending to the 3' end. Although the core protein region is well conserved and invariable, the envelope glycoproteins are hyper-variable.

Although humans infected with HCV generate an antibody response to the envelope glycoproteins, due to the hypervariability of these proteins, new variants are constantly generated that are not recognized by existing antibodies. As a consequence, most persons infected with HCV are not able to eliminate the virus and develop chronic infection that may go unrecognized for decades. Ultimately, the chronic infection of the liver leads to liver cirrhosis and hepatocellular carcinoma. The hypervariability of HCV surface glycoproteins and the high mutation rate of HCV complicate the development of a broad-based surface antigen vaccine. The present system for screening and development of antiviral agents directed to the invariate core protein, including those able to block the assembly of HCV, may be particularly useful given the high morbidity and ultimate mortality associated with HCV infection.

In the United States, an estimated 1.8% of the population, or 3.9 million individuals are infected with HCV. Liver disease resulting from HCV infection is responsible for approximately eight- to ten-thousand deaths annually. Within twenty years the number of deaths attributed to HCV infection is projected to triple. In the long term, the development of antiviral agents targeting invariable aspects of the virus, such as the highly conserved core or capsid proteins and/or their assembly into mature nucleocapsids will be needed to stem the projected HCV infection rates.

The present invention is directed to the development of antiviral agents for the treatment of hepatitis C virus infections and their benign and malignant sequelae by providing recombinant HCV capsid proteins that assemble in vitro to form large spherical virus-like particle ("LSVL") structures. Such structures have also been termed pseudo-capsids or pseudo-nucleocapsids herein. Such LSVL are a model of virus assembly and may be used for high throughput screening for agents able to affect virus assembly in vivo. In one embodiment, the invention provides genetic constructs that include a polynucleotide sequence encoding at least a portion of a eucaryotic virus capsid polypeptide wherein said polypeptide is able to participate in formation of a LSVL in vitro. As one example of such a construct, genetic constructs including polynucleotides encoding the human hepatitis C capsid polypeptide and truncated portions thereof are provided.

In one embodiment of the present invention, a eukaryotic virus pseudo-nucleocapsid is provided that includes at least a portion of a viral capsid polypeptide and a polynucleotide wherein the viral capsid polypeptide and a polynucleotide is formed in vitro. As one example of a pseudo-nucleocapsid formed according to the present invention, there is provided a LSVL formed by admixture of tRNA$_{phe}$ with a COOH terminal truncation variant of HCV having the amino acid sequence of SEQ ID NO.: 1. Those of skill in the art will be able to find not only the published sequence for the hepatitis C virus capsid protein and its variants, be also be able to select the best choice of coding preferences for each amino acid based on the preferred usage of organisms for amino acids.

The invention also provides a system for isolating antagonists or agonists of viral capsid assembly that includes the steps of; expressing a polynucleotide sequence encoding a recombinant viral capsid assembly polypeptide sequence in a archeal, prokaryotic, or eukaryotic host, purifying the viral capsid assembly polypeptide sequence, determining conditions enabling viral capsid or pseudo-nucleocapsid assembly in vitro, and admixing potential antagonists or agonists to the determined conditions and measuring enhancement or derogation of viral capsid or pseudo-nucleocapsid assembly. In one embodiment, the determining conditions enabling viral capsid or pseudo-nucleocapsid capsid assembly in vitro include determining the composition and quantity of a polynucleotide able to promote pseudo-nucleocapsid capsid assembly.

Also provided in one embodiment of the present invention is a system for isolating aptamers that may function to catalyze viral capsid assembly. The system includes the steps of: (a) synthesizing a random phosphodiester oligonucleotide library, (b) mixing the oligonucleotide library with a solution comprising one or more types of purified recombinant viral capsomer polypeptides, (c) separating pseudo-nucleocapsids formed, (d) amplifying oligonucleotides associated with the separated pseudo-nucleocapsids to create a selected oligonucleotide sub-library, and as necessary, (e) repeating steps (b)–(d) iteratively until an aptamer population of defined sequence is obtained.

The present invention provides a model for the isolation of aptamers able to catalyze the formation of LSVL. It is anticipated that the present system may be applied to the generation of aptamers able to catalyze the formation of LSVL of a large number of viruses. Such LSVL may be particularly useful in vaccine development against viruses, which are difficult to grow in cell culture or whose pathogenicity makes vaccine development hazardous.

In one embodiment, the present invention also provides a system for isolating aptamers that can function to agonize or antagonize viral capsid assembly, including the steps of: (a) synthesizing a random phosphodiester oligonucleotide library, (b) admixing the oligonucleotide library with a solution of recombinant viral capsid polypeptides, (c) isolating oligonucleotides bound to the viral capsid polypeptides, (d) amplifying oligonucleotides associated with the separated viral capsid polypeptides to create a selected oligonucleotide sub-library, (e) repeating steps (b)– (d) iteratively until an aptamer population of defined sequence is obtained; (f) admixing aptamers of defined sequence obtained a viral pseudo-capsid or nucelocapsid or the constituents thereof; and (g) determining which aptamers are able to agonize or antagonize viral pseudo-capsid or nucleocapsid formation.

According to the invention there is also provided a genetic construct that includes a nucleotide sequence encoding a hepatitis C virus capsid assembly amino acid sequence ("CAS"), which is inserted into a transfer vector and operatively expressed by a promoter of that vector. The construct may be adapted, using techniques known in the art, for expression of the HCV CAS in archeal, prokaryotic or eukaryotic cells In one embodiment, the HCV CAS is isolated from a wild type HCV capsid gene. In a particular embodiment, the HCV CAS includes a nucleic acid sequence that encodes the polypeptide sequence of SEQ ID NO.: 1. The genetic construct may further include other portions of the HCV genome.

According to another aspect of the invention, the invention provides a non-mammalian eukaryotic host cell transformed by the genetic constructs of the invention including HCV CAS according to SEQ. ID. NO.: 1, or truncations thereof. Yet another aspect of the invention is a method for producing a recombinant HCV capsid protein, assembled into a large spherical virus-like ("LSVL") particle structure or a portion thereof, including the steps of: (1) cloning a HCV gene that codes for the capsid protein into a transfer vector wherein the open reading frame of said gene is under the control of the promoter of said vector; (2) transferring the recombinant vector into a host cell, wherein the cloned HCV gene expresses the HCV capsid protein; and (3) isolating large spherical virus-like particles structures, that include the HCV capsid protein, from the host cell.

In one embodiment, the cloned hepatitis C virus gene has the conformational characteristics of the hepatitis C virus capsid coding sequence, and the expressed protein assembles into large spherical virus-like particles structures that include the capsid protein. In another embodiment, the cloning step further cloning a HCV gene coding for a truncated capsid protein, whereby said protein is expressed in the host cell and wherein the isolated LSVL particle include truncated capsid proteins. In one embodiment the transfer vector is the vaccinia virus. When a host cell is a mammalian cell, polyadenylation signals may be provided.

In another embodiment, the HCV capsid protein SEQ ID NO. 1 coding sequence is included in a vector in a host cell. The host cell into which the genetic construct is transfected may be, e.g., a prokaryotic or a eukaryotic cell. The transfer vector for use with the invention may be, e.g., a bacterial or a baculovirus based transfer vector. The hepatitis C virus capsid gene is under the control of a promoter that is selected based in its activity in the host cell.

In an alternative embodiment of the method of the invention, the transfer vector is a yeast transfer vector, and the recombinant vector is transfected into yeast cells. According to yet another aspect of the invention there is provided a virus large spherical virus-like particles structure, or a portion thereof, including hepatitis C virus capsid protein, produced by the method the invention. Alternatively, the virus large spherical virus-like particles structure can consist essentially of hepatitis C virus capsid proteins, produced by the method of the invention. In one particular embodiment, the virus large spherical virus-like particles structure includes a hepatitis C virus capsid protein that is the expression product of a capsid protein DNA cloned from a wild type virus. The virus capsids or large spherical virus-like particles structures of the invention, or portions or fragments thereof, may include of hepatitis C virus capsid protein. Alternatively, these capsids or large spherical virus-like particles structures or their fragments may include wild type hepatitis C virus capsid protein.

The virus capsid structures according to any of the methods of the invention include capsid proteins having immunogenic conformational epitopes capable of inducing neutralizing antibodies against native hepatitis C virus. In a preferred embodiment, the hepatitis C virus capsid protein is the expression product of a wild type HCV capsid gene.

According to yet another aspect of the invention there is provided a unit dose of a vaccine, comprising a peptide having conformational epitopes of a hepatitis C virus capsid protein, in an effective immunogenic concentration sufficient to induce a hepatitis C virus neutralizing antibody when administered according to an immunizing dosage schedule. In one embodiment, the vaccine comprises a portion of the capsid protein sufficient for a LSVL capsid particle to be formed. In one embodiment, the vaccine includes a portion of the HCV capsid protein that is a wild type HCV protein. Use of the HCV capsid open reading frame (ORF) from a wild type hepatitis C virus genome, according to the methods of the invention, particularly facilitates the production of preparative amounts of virus-like particles on a scale suitable for vaccine use.

According to yet another aspect of the invention is a method of preventing or treating hepatitis C virus infection in a vertebrate. The treatment regime includes administering hepatitis C virus large spherical virus-like particles structure or a fragment thereof to a vertebrate in a form and at a location that will maximize the immunogenicity of the particle. The treatment regimen will be designed to maximize the production of a cellular immune response as may be directed by the form, site and adjuvant used for inoculation.

The invention further provides a method of preventing or treating hepatitis C virus infection in a vertebrate, that includes the steps of, administering a hepatitis C virus large spherical virus-like particles structure of the invention, or a vaccine product comprising the large spherical virus-like particles structure to a vertebrate, according to an immunity-producing regimen.

Also within the scope of the invention is a method for immunizing a vertebrate against hepatitis C virus infection, that includes administering to the vertebrate a recombinant genetic construct of the invention including a conformational hepatitis C virus coding sequence, and allowing the coding sequence to be expressed in the cells or tissues of the vertebrate, whereby an effective, neutralizing, immune response to hepatitis C virus is induced.

According to yet another aspect of the invention, there is provided a method of detecting hepatitis C virus in a specimen from an animal suspected of being infected with the virus, including contacting the specimen with antibodies having a specificity to one or more conformational epitopes of the capsid of said hepatitis C virus. The antibodies have a detectable signal producing label or are attached to a detectably labeled reagent, allowing the antibodies to bind to the hepatitis C virus, and determining the presence of hepatitis C virus present in the specimen using a detectable label.

According to yet another aspect of the invention, there is provided a method of determining a cellular immune response to hepatitis C virus in an animal suspected of being infected with the virus, that includes contacting immuno-competent cells of said animal with a recombinant wild type hepatitis C virus capsid protein, or combined recombinant portion of a capsid protein according to the invention and assessing cellular or humoral immunity to hepatitis C virus by means of the proliferative response of said cells to the capsid protein. The recombinant hepatitis C virus protein may be introduced into the animal, e.g., subcutaneously. The terms "contacted" and "exposed", when applied to a cell, are used herein to describe the process by which a hepatitis C viral capsid protein or large spherical virus-like particle is delivered to a target cell or is placed in direct juxtaposition with the target cell.

A hepatitis C virus infection diagnostic kit is also a part of the invention. The diagnostic kit may include large spherical virus-like particles structures that include the hepatitis C virus capsid protein, large spherical virus-like particles structures that include hepatitis C virus proteins and capsid proteins or antibodies to either of these large spherical virus-like particles structures, singly or in combination, together with materials for carrying out an assay for humoral or cellular immunity against hepatitis C virus, in a unit package container.

DETAILED DESCRIPTION OF THE INVENTION

While the making and using of various embodiments of the present invention are discussed in detail below, it should be appreciated that the present invention provides many applicable inventive concepts that may be embodied in a wide variety of specific contexts. The specific embodiments discussed herein are merely illustrative of specific ways to make and use the invention and do not delimit the scope of the invention.

The present invention stems from a program to determine the structure of hepatitis C virus (HCV) core protein or proteins that are bound to the viral RNA sequence essential for genome encapsidation. These structural results are pivotal for the rational design of oligonucleotide mimetics that will interfere with HCV genome recognition and packaging. The HCV core protein (amino acids 1–191) and C-terminally truncated core proteins were expressed in bacterial cells.

In one example, a truncated core protein HCVC-124 (corresponding to amino acids 2–124) and HCVC-179 (corresponding to amino acids 2–179) has been purified in milligram quantities. Spectroscopic (i.e., CD, fluorescence, NMR), and analytical ultracentrifugation and X-ray crystallographic studies were conducted to determine the structure and solution properties of HCVC-124. Purified HCV core protein may be used, e.g., in a PCR-based in vitro selection assay to identify the viral RNA encapsidation sequence. Purified HCV core protein-will be incubated with the viral-based RNA aptamers, and used in X-ray crystallographic studies to determine the structure of HCV core bound to RNA. The following definitions are used to define terms that will be used throughout the specification.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

As used throughout the present specification the following abbreviations are used: TF, transcription factor; ORF, open reading frame; kb, kilobase (pairs); UTR, untranslated region; kD, kilodalton; PCR, polymerase chain reaction; RT, reverse transcriptase; LVSL, large spherical virus-like particles.

The term "LVSL" is used interchangeably herein with pseudo-capsid or pseudo-nucleocapsid. The term "capsid"

refers to the protein shell that encloses the viral nucleic acid. The capsid is built of polypeptide units that cluster to form the morphological units seen by electron microscopy on the surface of particles and termed "capsomers." The capsid together with its enclosed nucleic acid is called the "nucleocapsid."

Proteins are most easily characterized by their amino acid sequence or primary structure. Proteins typically develop intra and intermolecular relationships to form secondary, tertiary and quaternary structures. A protein's secondary structure is the three dimensional structure of constitutant segments the protein (for example, an alpha helix, or a beta-sheet, or a beta-turn). Tertiary structure may be formed by virtue of interactions between secondary structural elements as well as between amino acid side chains between amide bonds, of the protein. Proteins may also self-assemble, or alternatively, assemble with heterologous proteins into a quaternary structure. The amino acid sequence of the HCV core protein is an example of primary structure. The three-dimensional spheroid assembly of HCV capsid or core proteins together with polynucleotide sequences into a "pseudo-nucleocapsid" is an example of quaternary structure.

The term "hepatitis C capsid protein" refers to the polypeptide as set forth (SEQ ID NO.:1) or a nucleic acid sequence that encodes the protein essentially as set forth (SEQ ID NO.:1).

(e.g., Southern or Northern blot, solution hybridization and the like) under conditions of low stringency. Low stringency conditions may be used to identify the binding of two sequences to one another while still being specific (i.e., selective). The absence of non-specific binding may be tested by the use of a second target that lacks even a partial degree of complementarity (e.g., less than about 30% identity). In the absence of non-specific binding, the probe will not hybridize to the second non-complementary target and the original interaction will be found to be selective.

Low stringency conditions are generally conditions equivalent to binding or hybridization at 42 degrees Centigrade in a solution consisting of 5XSSPE (43.8 g/l NaCl, 6.9 g/l $NaH_2PO_4$—$H_2O$ and 1.85 g/l EDTA, pH 7.4), 0.1% SDS, 5×Denhardt's reagent (50×Denhardt's contains per 500 ml: 5 g Ficoll (Type 400, Pharmacia), 5 g BSA (Fraction V; Sigma) and 100 micrograms/ml denatured salmon sperm DNA); followed by washing in a solution comprising 5×SSPE, 0.1% SDS at 42 degrees Centigrade when a probe of about 500 nucleotides in length is employed.

The art knows that numerous equivalent conditions may be employed to achieve low stringency conditions. Factors that affect the level of stringency include: the length and nature (DNA, RNA, base composition) of the probe and nature of the target (DNA, RNA, base composition, present in solution or immobilized, etc.) and the concentration of the salts and other components (e.g., formamide, dextran

```
MSTNPKPQRL TCRNTNRRPQ DVKFPGGGQI VGGVYLLPRR GPRLGVRATR KTSERSNPRG

RRNPIPKARR PDGRTWANPG YPWPLYGNEG CGWAGWLLSP RGSRPSWGPT DPWRRSRNLG

KVIDTLTCGF ADLMGYIPLV GAPLGGAARA LAHGVRVLED GVNYATGNLP GCSFSIFLLA

LLSCLTVPAS A
```

The terms "a sequence essentially as set forth in SEQ ID NO. (#)", "a sequence similar to", "nucleotide sequence" and similar terms, with respect to nucleotides, refers to sequences that substantially correspond to any portion of the polypeptide sequence identified herein as SEQ ID NO.: 1. These terms refer to synthetic as well as naturally-derived molecules and includes sequences that possess biologically, immunologically, experimentally, or otherwise functionally equivalent activity, for instance with respect to hybridization by nucleic acid segments, or the ability to encode all or portions of a hepatitis C capsid protein. Naturally, these terms are meant to include information in such a sequence as specified by its linear order.

The term "sequence similarity" refers to the extent to which two nucleic acids are complementary. There may be partial or complete sequence similarity. A partially complementary sequence is one that at least partially inhibits a completely complementary sequence from hybridizing to a target nucleic acid and is referred to using the functional term "substantially similar." The degree or extent of hybridization may be examined using a hybridization or other assay (such as a competitive PCR assay) and is meant, as will be known to those of skill in the art, to include specific interaction even at low stringency. In the context of the present invention, a functional similarity is found when the construct is capable of participating in formation of a LSVL in vitro.

The inhibition of hybridization of the completely complementary sequence to the target sequence may also be examined using a hybridization assay involving a solid support sulfate, polyethylene glycol). Likewise, the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, inclusion of formamide, etc.).

An oligonucleotide sequence that is "substantially similar" to the hepatitis C capsid protein gene is defined herein as an oligonucleotide sequence that exhibits greater than or equal to 60% identity to the sequence of the hepatitic C capsid protein gene, when sequences having a length of 100 bp or larger are compared. Substantial similarity may also be observed for sequences that form a functional capsid protein that is able to participate in formation of a LSVL in vitro.

The term "gene" is used to refer to a functional protein, polypeptide or peptide-encoding unit. As will be understood by those in the art, this functional term includes genomic sequences, fragments or combinations thereof, as well as gene products, including those that may have been altered by the hand of man. Purified genes, nucleic acids, protein and the like are used to refer to these entities when identified and separated from at least one contaminating nucleic acid or protein with which it is ordinarily associated.

As used herein, the term "vector" is used in reference to nucleic acid molecules that transfer DNA segment(s) from one cell to another. The vector may be further defined as one designed to propagate hepatitis C capsid protein sequences, or as an expression vector that includes a promoter operatively linked to the hepatitis C capsid protein sequence, or one designed to cause such a promoter to be introduced. The vector may exist in a state independent of the host cell chromosome, or may be integrated into the host cell chromosome The term "recombinant" in the context of polypeptide coding regions and the polypeptides encoded by such coding regions refers to non-native products wherein the coding regions, and typically the expression thereof, have been manipulated in vitro by man to differ from their occurrence in nature. The viral capsid polypeptides of the present invention may be produced in a number of different recombinant systems as known in the art including archeal, prokaryotic, or eukaryotic. For examples not limiting on the intended expression systems that may be utilized, bacterial, yeast, baculovirus, and mammalian vectors and corresponding host organisms may be utilized according to methods known in the art. For expression in an appropriate expression system, the desired viral capsid polypeptide coding regions are operably linked into an expression vector and introduced into a host cell to enable expression. The coding region with the appropriate regulatory regions will be provided in proper orientation and reading frame to allow for expression. Methods for gene construction are known in the art. See, in particular, Molecular Cloning, A Laboratory Manual, Sambrook et al, eds., Cold Spring Harbor Laboratory, Second Edition, Cold Spring Harbor, N.Y. (1989) and the references cited therein.

Where post-translational modification may be required for generating proteins of appropriate conformation, eucaryotic systems may be employed. Where desired, a baculovirus system known in the art may offer rapid cloning and high levels of expression including eucaryotic mechanisms for processing of proteins such as glycosylation and phosphorylation. See, for example, Smith, et al., Mol. Cell Biol. (1985) 3:2156–2165.

The term "host cell" refers to cells that have been engineered to contain nucleic acid segments of the hepatitis C capsid protein, or altered segments, whether archeal, prokaryotic, or eukaryotic. Thus, engineered, or recombinant cells, are distinguishable from naturally occurring cells that do not contain recombinantly introduced genes through the hand of man.

The term "agonist" refers to a molecule that enhances either the strength or the time of an effect of hepatitis C capsid protein and encompasses small molecules, proteins, nucleic acids, carbohydrates, lipids, or other compounds. The term "antagonist" refers to a molecule that decreases either the strength or the time of an effect of hepatitis C capsid protein and encompasses small molecules, proteins, nucleic, acids, carbohydrates, lipids, or other compounds.

The term "altered", or "alterations" or "modified" with reference to nucleic acid or polypeptide sequences is meant to include changes such as insertions, deletions, substitutions, fusions with related or unrelated sequences, such as might occur by the hand of man, or those that may occur naturally such as polymorphisms, alleles and other structural types. Alterations encompass genomic DNA and RNA sequences that may differ with respect to their hybridization properties using a given hybridization probe. Alterations of polynucleotide sequences for hepatitis C capsid protein, or fragments thereof, include those that increase, decrease, or have no effect on functionality. Alterations of polypeptides refer to those that have been changed by recombinant DNA engineering, chemical, or biochemical modifications, such as amino acid derivatives or conjugates, or post-translational modifications.

The present invention is a process for generating large spherical virus-like (LSVL) particles from purified recombinant viral capsid proteins. In one embodiment of the present invention, LSVL particles are generated from purified recombinant hepatitis C virus (HCV) capsid proteins. The LSVL may be used as immunogens presenting capsid protein epitopes including epitopes existing as a consequence of the assembly of individual capsid polypeptides into a quaternary structure. The LSVL particles generated may be used in assays to identify inhibitors of viral assembly or disassembly, including in one embodiment, HCV assembly or disassembly. These assays are readily adapted to the high-throughput library-screening format favored by many pharmaceutical companies. Inhibitors of viral assembly or disassembly are potential antiviral agents. Inhibitors of viral assembly, "antagonists", may be expected to interfere with the formation of new virus particles or the completion of the viral replication cycle. Inhibitors, of viral disassembly, "agonists", may be expected to interfere with the uncoating of virus particles as they infect the cell thus preventing the encapsidated viral genome from initiating viral replication. Furthermore, inhibitors of viral disassembly, "agonists", may be expected to be useful in stabilizing the quaternary structure of viral pseudo-capsids such that when used in assays or as vaccines, they have prolonged self-life in vitro and have a prolonged biological half-life in vivo after administration. Where pseudo-capsids are used as gene delivery agents for in vivo gene transfer, the present system for the selection and isolation of inhibitors of viral disassembly may be of particular utility.

The process of the present invention is used to generate LSVL particles, which may be incorporated into assays used to identify inhibitors of viral assembly and disassembly. Furthermore, it is intended that the system of the present invention may be adapted for use with other viruses.

Expression and Purification of Capsid Protein Variants

The system disclosed herein begins with the expression and purification of recombinant variants of the HCV capsid protein. The expressed protein variants are HCV capsid proteins that are assembled into large spherical virus-like (LSVL) particles. Intermolecular contacts within the LSVL particles may be similar to those that exist in the intact native virion. Assembly of LSVL particles is achieved by incubating recombinant HCV capsid protein with nucleic acids, e.g., oligonucleotides such as transfer RNA (tRNA).

The formation of LSVL particles in vitro is useful for the development of high throughput assays to identify inhibitors of HCV assembly and disassembly. Compounds that suppress the formation of LSVL particles are potential inhibitors of HCV assembly ("antagonists"). Compounds that increase the formation of LSVL particles are potential inhibitors of HCV disassembly ("agonists"). The assembly of LSVL particles may be quantitated for example by a number of biochemical and biophysical methods, among them electron microscopy, velocity sedimentation, fluorescence emission, fluorescence polarization, and solution scattering. Since LSVL assembly may be monitored spectroscopically, the assembly of LSVL particles in high-throughput library screens may be monitored using available instrumentation (e.g., 96-well plate spectrofluorometers).

In operation, compounds from a chemical library are added to each well of a 96-well plate and the fluorescence polarization (excitation wavelength 290 nm, emission wavelength 335 nm) in each well is recorded. Recombinant HCV capsid proteins are added to each well and the fluorescence polarization measurement repeated. Increased polarization (relative to a control well) would highlight compounds that promote HCV capsid assembly, and hence are potential inhibitors of HCV disassembly. Finally, tRNA is added to each well and the fluorescence polarization measurement repeated. Decreased polarization (relative to a control well) would highlight compounds that interfere with capsid assembly, and hence are potential inhibitors of HCV assembly. Thus, screening for inhibitors of assembly and disassembly would occur concurrently. As will be apparent to those of skill in the art, the present invention includes changing the order of the above steps so long as they do not affect the measured outcome of the present invention in high or even low throughput assay systems.

The present invention includes the designed and developed protocols for the expression, purification and solubilization of at least one recombinant HCV capsid protein. The system that was designed and developed, includes protocols for the in vitro assembly of recombinant HCV capsid protein. The assembly system developed was adapted for use in high-throughput library screening for inhibitors of HCV assembly.

An important feature of the present invention is the use of truncated HCV capsid protein (for example, the HCVC124 isolate includes only 65% of the native protein structure). Using the truncated capsid protein, large spherical particles (50–200 nm in diameter) were generated that were amenable to characterization by light scattering and absorbance measurements. Furthermore, the LSVL particles form the basis of assays to identify inhibitors of HCV assembly and/or disassembly spontaneously formed in vitro.

The expression, purification and solubilization of HCVC124 is described as follows. A recombinant protein was generated using standard molecular biologic techniques that includes residues 1 to 124 of the HCV capsid protein. Coomassie blue-staining of an SDS-polyacrylamide gel showed that the purification of HCVC124 was successful (data not shown).

Cells from the glycerol stocks of the HCVC124 expressing isolate were grown overnight in 2xYT/Kan media at 37° C., 300 rpm. The next morning the overnight culture was used to inoculate fresh 2xYT/Kan media. Typically, a 10 mL overnight culture was used to inoculate 500 mL uninduced culture. The inoculated culture was grown at 37° C., 300 rpm to an $OD_{600}$ of ~0.6 to ~0.8.

Next, protein expression was induced with 1 mM IPTG, followed by a three (3) hour incubation at 24° C. (room temperature), 300 rpm. The cells were pelleted and frozen at −70° C. Next, the cell pellet was resuspended in 35 mL urea lysis buffer per 1L culture and sonicated. Urea lysis buffer is: 8M Urea (pretreated with Dowex MR-3 beads: 1 g beads per 100 mL solution), 25 mM Na phosphate pH 7.0, 250 mM NaCl, 2 mM EDTA, 2 mM DTT. The sonicated sample was centrifuged at 4° C. for 20 minutes in the SS-34 rotor at 50,000×g.

The supernatant was removed and saved at 4° C. for cation exchange purification. The lysis pellet was resuspended again in urea lysis buffer and sonicated and centrifuged. The supernatant was saved for cation exchange. The supernatant was loaded on a cation exchange column (POROS 20 CM) equilibrated with 25 mM HEPES pH 7.0, 8 M urea. Protein was eluted with a linear gradient of NaCl (150 mM NaCl to 675 mM NaCl over 10 column volumes. Fractions containing HCV capsid protein were pooled. Pooled sample was dialyzed overnight at 4° C. against refolding buffer (20 mM Tris pH 7.0, 150 mM NaCl, 5 mM DTT) and then concentrated.

A concentrated sample was loaded on a C18 reverse-phase column (ODS-18) equilibrated with 20 mM NaPhos pH 3.0 and eluted with a linear gradient of methanol. Fractions containing HCV capsid protein were pooled, dialysed o/n, 4° C., against refolding buffer (20 mM Tris pH 7.0, 150 mM NaCl, 5 mM DTT) and protease inhibitors were added to final concentrations 0.05 mM Leupeptin (10 mM stock), 0.001 mM Pepstatin A (1 mM stock), 0.5 mM PMSF (100 mM stock)and then concentrated.

Production of Full-length and Core Protein Variants for Encapsidation Determinations The minimal viral RNA sequence necessary for the specific and high-affinity binding to HCV core protein may be determined using the assembly system. Analogous to other enveloped RNA viruses, the packaging of HCV genome with core protein and the subsequent assembly of the nucleoprotein capsid are believed to be initiated by specific and high-affinity binding of core protein to an RNA encapsidation sequence. Essential or preferential encapsidation sequences may be determined using PCR-based in vitro selection against purified HCV core protein.

Using the truncated HCV protein variants, cocrystallization trials of the HCV core protein complexed with the RNA encapsidation sequence may be conducted. Purified HCV core protein is incubated with RNA oligonucleotides containing the encapsidation sequence and used to generate protein crystals for x-ray crystallographic studies.

More specifically, an *E. coli* pET30 vector (Novagen) encoding the HCV core protein was constructed using the polymerase chain reaction (PCR) methods from a template cDNA encoding capsid protein from HCV (strain AG94, genotype 1a). The cDNA was obtained from Dr. Stanley Lemon, UTMB Galveston. For one example of the optimization of protein expression and solubility, two HCV core protein variants were created and analyzed. The predicated protein sequence of HCV core protein is shown in FIG. 1*a*. Underlined residues correspond to highly hydrophobic regions (calculated using Kyte-Dolittle parameters). Highlighted residues correspond to the carboxy terminus of the five proposed HCV core protein variants. FIG. 1*a–e* shows the amino-acid sequences of these five variants: the full-length core protein (residues 1–191, 20.7 kD, SEG. ID. No.: 1), and carboxy terminus truncated variants Δ12 (residues 1–179, 19.6 kD, SEQ ID NO.: 1), and Δ67 (residues 1–124, 13.7 kD). Truncated core variants were chosen to either eliminate the long hydrophobic stretches of the protein (constructs Δ67) or to optimize protein expression (construct Δ12 and Δ67). DNA sequencing was conducted to confirm the authenticity of all constructs. These constructs were used to transform competent B21(DE3) cells for IPTG-induced expression of recombinant protein.

The recombinant core protein and the truncated variants have calculated isoelectric points of approximately 11.5. Given the high pI of the core protein relative to *E. coli* proteins, cation exchange chromatography may be used if desired to purify core protein from both the soluble and insoluble fractions of the bacterial lysate resulting in substantial purification. Further purification may be performed using additional HPLC columns. Urea denatured core protein, purified from the insoluble fraction of the bacterial cell lysate, may be refolded by dialysing against physiological buffers. The oligomeric and aggregation state of HCV core proteins may be determined using one or more analytical techniques including gel filtration chromatography, dynamic light scattering and analytical ultracentrifugation. The existence of a folded domain may be assayed by tryptic digest. Circular dichroism (CD) spectroscopy may be used to quantitate the degree of secondary structure in these proteins.

Commercially available crystallization buffers (Hampton Research) may be employed to examine a wide variety of solution conditions to generate crystals of purified HCV core protein constructs. X-ray diffraction data may be collected for example using MacScience DIP2030 type detectors or Bruker CCD-based type detectors.

A cDNA corresponding to the HCV genome may be used as a template for a modified "whole genome PCR" strategy to generate a large number of cDNA fragments that completely span the viral genome. These cDNA fragments are transcribed into RNA and incubated with HCV core protein. Sequences that bind protein may be selected using a filter-binding protocol. Since the filter selectively binds protein, RNA eluted from the filter will form an enriched sequence pool with affinity for core protein. The RNA is reverse transcribed, PCR amplified, transcribed and subjected to 2–10 cycles of increasingly stringent selection (achieved through using limiting protein concentrations). In the final cycle, the amplified PCR products are cloned into *E. coli* and 10–20 colonies sequenced to identify a consensus binding site. Gel shift assays may be used to quantitate the binding affinity between the corresponding RNA sequence and all soluble HCV core protein variants.

Generation of LSVL Particles from Purified Recombinant HCVC124

Nucleocapsid pseudo-particles are generated by mixing purified recombinant core protein or core protein truncation variants with RNA under defined conditions. In one example, purified recombinant HCV capsid protein (HCVC124) was diluted in assembly buffer (100 mM KAcetate, 1.7 mM MgAcetate, 25 mM HEPES pH 7.4, 5 mM DTT) to a final concentration of approximately 1 mg/ml Or 0.1 mM. Oligonucleotides (e.g., $tRNA_{phe}$, SIGMA) are resuspended in assembly buffer to a final relative ratio of 1/10 nucleotide to protein concentration. These amounts were found to be an example of an effective protein polynucleotide ratio. Equal volumes of the capsid protein and the RNA solutions were mixed together and incubated at 30° C. for 10 minutes prior to transfer to 4° C. for at least approximately 15 minutes before analysis. Electron microscopy of negative stained preparations comprising the mixture of HCVC124 capsid protein and tRNA showed the formation of spheroid LSVL particles (data not shown).

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. An isolated virus pseudo-nucleocapsid consisting of:
   a viral capsid polypeptide, wherein the viral capsid polypeptide is SEQ ID NO.: 1; and
   a tRNA molecule, wherein said viral capsid polypeptide and tRNA molecule together participate in formation of a generally spheroid pseudo-nucleocapsid in vitro.

2. The virus pseudo-nucleocapsid of claim 1, wherein said virus pseudo-nucleocapsid is formed in an in vitro array.

3. The virus pseudo-nucleocapsid of claim 1, wherein said viral capsid polypeptide is a recombinant polypeptide.

4. The virus pseudo-nucleocapsid of claim 1, wherein said tRNA molecule is selected from the group consisting of hepatitis C virus genome and flavivirus genome.

5. The virus pseudo-nucleocapsid of claim 1, wherein said virus pseudo-nucleocapsid is formed in an insect cell host.

6. The virus pseudo-nucleocapsid of claim 1, wherein said virus pseudo-nucleocapsid is formed in an Sf-9 insect cell.

7. The virus pseudo-nucleocapsid of claim 1, wherein said virus pseudo-nucleocapsid is formed in a mammalian cell host.

8. The virus pseudo-nucleocapsid of claim 1, wherein said virus pseudo-nucleocapsid is formed in a yeast cell host.

9. An isolated virus pseudo-nucleocapsid consisting of:
   a recombinant viral capsid polypeptide, wherein the recombinant viral capsid polypeptide is SEQ ID NO.: 1; and
   a tRNA molecule, wherein said recombinant viral capsid polypeptide and tRNA molecule together participate in the formation of a generally spheroid pseudo-nucleocapsid in vitro.

10. An isolated virus pseudo-nucleocapsid consisting of:
    a recombinant viral capsid polypeptide, wherein the recombinant viral capsid polypeptide is SEQ ID NO.: 1; and
    a tRNA molecule, wherein said recombinant viral capsid polypeptide and tRNA molecule together participate in the formation of a generally spheroid pseudo-nucleocapsid an in vitro array;
    wherein the virus pseudo-nucleocapsid is formed in an in vitro array.

11. A method of preparing a virus pseudo-nucleocapsid consisting of:
    contacting a viral capsid polypeptide with a tRNA molecule, wherein the viral capsid polypeptide is SEQ ID NO.: 1; and
    allowing said viral capsid polypeptide and tRNA molecule to participate in the formation of a generally shperoid pseudo-nucleocapsid in vitro.

12. A method of preparing a virus pseudo-nucleocapsid consisting of:
    contacting a recombinant viral capsid polypeptide with a tRNA molecule, wherein the recombinant viral capsid polypeptide is SEQ ID NO.: 1; and
    allowing said recombinant viral capsid polypeptide and tRNA molecule to participate in the formation of a generally spheroid pseudo-nucleocapsid in vitro.

13. A method of preparing a virus pseudo-nucleocapsid consisting of:
    contacting a viral capsid polypeptide with a tRNA molecule, wherein the viral capsid polypeptide is SEQ ID NO.: 1; and
    allowing said viral capsid polypeptide and tRNA molecule to participate in the formation of a generally spheroid pseudo-nucleocapsid in vitro, wherein the virus pseudo-nucleocapsid is formed in an in vitro array.

* * * * *

SEQUENCE LISTING

<160> NUMBER OF SEQ ID NOS: 1

<210> SEQ ID NO 1
<211> LENGTH: 191
<212> TYPE: PRT
<213> ORGANISM: Hepatitis C virus

<400> SEQUENCE: 1

```
Met Ser Thr Asn Pro Lys Pro Gln Arg Leu Thr Cys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Asn Pro Arg Gly Arg Arg Asn Pro
    50                  55                  60

Ile Pro Lys Ala Arg Arg Pro Asp Gly Arg Thr Trp Ala Asn Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Trp Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160
```

-continued

```
Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
            180                 185                 190
```